United States Patent

Doughty et al.

[11] Patent Number: 5,871,760
[45] Date of Patent: Feb. 16, 1999

[54] SKIN CARE COMPOSITIONS

[75] Inventors: Darrell Gene Doughty; Joseph Anthony Gatto, both of Cincinnati, Ohio; Zahid Nawaz, Buckinghamshire; Richard George A. Rolls, Middlesex, both of Great Britain

[73] Assignee: The Procter & Gamble Company, Cinncinnati, Ohio

[21] Appl. No.: 849,181

[22] PCT Filed: Oct. 30, 1995

[86] PCT No.: PCT/US95/13981

§ 371 Date: May 28, 1997

§ 102(e) Date: May 28, 1997

[87] PCT Pub. No.: WO96/16545

PCT Pub. Date: Jun. 6, 1996

[30] Foreign Application Priority Data

Nov. 28, 1994 [GB] United Kingdom ............ 9423974

[51] Int. Cl.[6] .................................................. A61K 7/48
[52] U.S. Cl. ......................... 424/401; 514/844; 514/937
[58] Field of Search ............. 424/401; 514/937, 514/844

[56] References Cited

U.S. PATENT DOCUMENTS 5,334,372  8/1994  Kawamata et al. ............... 424/78.03
5,417,967  5/1995  Kawamata et al. ............... 424/78.03
5,599,800  2/1997  Candau et al. ...................... 514/53

OTHER PUBLICATIONS

Date et al. Chemical Abstracts, vol. 122, #38547, 1994.
Date et al. Chemical Abstracts, vol. 121 #212639, 1994

*Primary Examiner*—Jyothsna Venkat
*Attorney, Agent, or Firm*—Loretta J. Henderson; T. David Reed

[57] ABSTRACT

A skin care composition in the form of an oil-in-water dispersion which comprises from about 1% to about 60% oil phase components including from about 0.01% to about 20% by weight of a liquid, polyol carboxylic acid ester having a polyol moiety and at least 4 carboxylic acid moieties, wherein the polyol moiety is selected from the group consisting of sugars and sugar alcohols containing from about 4 to about 8 hydroxyl groups, and wherein each carboxylic acid moiety has from about 8 to about 22 carbon atoms, and wherein said liquid polyol carboxylic acid ester has a complete melting point of less than about 30° C., from about 30% to about 98.89% by weight of water, and from about 0.1% to about 20% of an organic amphiphilic emulsifier material which is capable of forming liquid crystals in product or on the skin. The composition provides improved moisturization, skin feel and skin care benefits and reduced greasiness, together with excellent rub-in, absorption and stability characteristics.

23 Claims, No Drawings

SKIN CARE COMPOSITIONS

TECHNICAL FIELD

The present invention relates to cosmetic compositions. In particular it relates to cosmetic compositions in the form of emulsions or lotions which provide improved moisturization, skin feel, skin care and appearance benefits and reduced greasiness, together with excellent rub-in and absorption characteristics. The compositions also display excellent stability characteristics at normal and elevated temperatures.

BACKGROUND OF THE INVENTION

Skin is made up of several layers of cells which coat and protect the keratin and collagen fibrous proteins that form the skeleton of its structure. The outermost of these layers, referred to as the stratum corneum, is known to be composed of 25 nm protein bundles surrounded by 8 mn thick layers. Anionic surfactants and organic solvents typically penetrate the stratum corneum membrane and, by delipidization (i.e. removal of the lipids from the stratum corneum), destroy its integrity. This destruction of the skin surface topography leads to a rough feel and may eventually permit the surfactant or solvent to interact with the keratin, creating irritation.

It is now recognised that maintaining the proper water gradient across the stratum corneum is important to its functionality. Most of this water, which is sometimes considered to be the stratum corneum's plasticizer, comes from inside the body. If the humidity is too low, such as in a cold climate, insufficient water remains in the outer layers of the stratum corneum to properly plasticize the tissue, and the skin begins to scale and becomes itchy. Skin permeability is also decreased somewhat when there is inadequate water across the stratum corneum. On the other hand, too much water on the outside of the skin causes the stratum corneum to ultimately sorb three to five times its own weight of bound water. This swells and puckers the skin and results in approximately a two to three fold increase in the permeability of the skin to water and other polar molecules.

Thus, a need exists for compositions which will assist the stratum corneum in maintaining its barrier and water-retention functions at optimum performance in spite of deleterious interactions which the skin may encounter in washing, work, and recreation.

Conventional cosmetic cream and lotion compositions as described, for example, in Sagarin, Cosmetics Science and Technology, 2nd Edition, Vol.1, Wiley Interscience (1972) and Encyclopaedia of Chemical Technology, Third Edition, Volume 7 are known to provide varying degrees of emolliency, barrier and water-retention (moisturizing) benefits. However, they can also suffer serious negatives in terms of skin feel (i.e. they often feel very greasy on the skin) as well as having poor rub-in, absorption and residue characteristics.

The present invention therefore provides skin-care cosmetic compositions which provide improvements in moisturization, absorption, skin feel, skin care and appearance characteristics and which in particular provide improved short and longer term moisturizing effectiveness, while at the same time reducing stickiness and avoiding a greasy feel on the skin. The compositions also display excellent stability characteristics at both normal and elevated temperatures.

SUMMARY OF THE INVENTION

According to one aspect of the present invention there is provided a skin care composition in the form of an oil-in-water emulsion comprising:

(a) from about 1% to about 60% by weight of oil phase components including from about 0.01% to about 20% by weight of a liquid, polyol carboxylic acid ester having a polyol moiety and at least 4 carboxylic acid moieties, wherein the polyol moiety is selected from sugars and sugar alcohols containing from about 4 to about 8 hydroxyl groups, and wherein each carboxylic acid moiety has from about 8 to about 22 carbon atoms, and wherein said liquid polyol carboxylic acid ester has a complete melting point of less than about 30° C.;

(b) from about 30% to about 98.89% by weight of water; and (c) from about 0.1% to about 20% by weight of an organic liquid crystal-forming amphiphilic emulsifier material.

DETAILED DESCRIPTION OF THE INVENTION

The compositions of the present invention take the form of an oil-in-water emulsion or dispersion containing one or more distinct emulsified or dispersed oil phases together with a skin conditioning agent and an essential liquid crystal-forming emulsifier component as well as various optional ingredients as indicated below. All levels and ratios are by weight of total composition, unless otherwise indicated. Chain length and degrees of ethoxylation are also specified on a weight average basis.

The term "skin conditioning agent", as used herein means a material which provides a "skin conditioning benefit". As used herein, the term "skin conditioning benefit" means to provide a therapeutic or cosmetic benefit to the skin including, but not limited to, moisturization, humectancy (i.e. the ability to retain or hold water or moisture in the skin), emolliency, visual improvement of the skin surface, soothing of the skin, softening of the skin, healing of minor cuts, abrasions and burns of the skin, and the like. The foregoing terms are all included under skin conditioning because a skin conditioning agent can provide one or more of these enumerated and other related benefits.

The term "complete melting point", as used herein means a melting point as measured by the well-known technique of Differential Scanning Calorimetry (DSC). The complete melting point is the temperature at the intersection of the baseline, i.e. the specific heat line, with the line tangent to the tralining edge of the endothermic peak. Typically a scanning temperature of 5° C./minute is used in the present invention in measuring the complete melting points. A technique for measuring complete melting points is more fully described in U.S. Pat. No. 5,306,514, to Letton et al., issued, Apr. 26, 1994.

The term "nonocclusive" as used herein, means that the component as so described does not obstruct the skin surface or block the passage of circulation of air and moisture.

A first essential component of the compositions herein is an oil or mixture of oils. In physical terms, the compositions generally take the form of a dispersion of one or more oil phases (referred to herein as primary phase, secondary phase,etc) in an aqueous continuous phase, each oil phase comprising a single oily component or a mixture of oily components in miscible or homogeneous form. The overall level of oil phase components in the compositions of the invention is preferably from about 1% to about 60%, preferably from about 2% to about 30% and more preferably from about 3% to about 20% by weight. In preferred embodiments, the primary oil phase is present in an amount of from about 4% to about 16%, more preferably from about 7% to about 15% by weight of composition. The level of primary oil phase component is found to be valuable herein for achieving optimum moisturization and greasiness characteristics. The primary oil phase generally comprises a natural or synthetic oil selected from mineral, vegetable, and animal oils, fats and waxes, fatty acid esters, fatty alcohols, fatty acids and mixtures thereof having emollient cosmetic properties. The primary oil phase component is preferably essentially silicone-free, ie contains no more than about 10%, preferably no more than about 5% by weight of silicon-based materials. It will be understood that the oil phase may contain small levels (eg. up to about 25%, preferably 10%) of oil phase soluble emulsifier ingredients. Such ingredients are not to be considered as oil phase components from the viewpoint of determining the oil phase level and required HLB. In preferred embodiments, the overall required HLB of the oil phase is from about 8 to about 12, especially from about 9 to about 11, required HLB being determined by summing the individual required HLB values for each component of the oil phase multiplied by its W/W percentage in the oil phase (see ICI Literature on HLB system).

Suitable primary oil phase components for use herein include, for example, optionally hydroxy-substituted $C_8$–$C_{50}$ unsaturated fatty acids and esters thereof, $C_1$–$C_{24}$ esters of $C_8$–$C_{30}$ saturated fatty acids such as isopropyl myristate, isopropyl palmitate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum and squalane, fatty sorbitan esters (see U.S. Pat. No. 3,988,255, Seiden, issued Oct. 26, 1976), lanolin and lanolin derivatives, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, shea butter, shorea butter, and sunflower seed oil and $C_1$–$C_{24}$ esters of dimer and trimer acids such as diisopropyl dimerate, diisostearylmalate, diisostearyldimerate and triisostearyltrimerate. Of the above, highly preferred are the mineral oils, petrolatums, unsaturated fatty acids and esters thereof and mixtures thereof.

Compositions herein preferably also comprise a secondary oil phase which in preferred embodiments is present in a level of from about 0.1% to about 20%, especially from about 0.1% to about 10% by weight of composition. Moreover, the primary oil phase is preferably present in weight excess of the secondary oil phase. The secondary oil phase component is preferably silicone-based. Suitable silicone components herein include water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof. In preferred embodiments the silicone component is a silicone gum having a molecular weight of from about 200,000 to about 4,000,000 or a mixture of silicones including the silicone gum. In mixtures, the silicone gum preferably constitutes from about 5% to about 40%, especially from about 10% to 20% by weight of the silicone mixture. The silicone or silicone mixture preferably constitutes from about 0.1% to about 20%, more preferably from about 0.1% to about 15%, and especially from about 0.1% to about 10% by weight of composition.

A preferred silicone component for use herein consists essentially of:

(i) a silicone having a molecular weight of from about 200,000 to about 4,000,000 selected from dimethiconol, fluorosilicone and dimethicone and mixtures thereof; and (ii) a silicone-based carrier having a viscosity from about 0.65 $mm^2.s^{-1}$ to about 100 $mm^2.s^{-1}$, wherein the ratio of i) to ii) is from about 10:90 to about 20:80 and wherein said silicone component has a final viscosity of from about 500 $mm^2.s^{-1}$ to about 10,000 $mm^2.s^{-1}$.

Dimethiconol-based silicones suitable for use herein have the chemical structure (II):

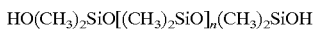

where n is from about 2000 to about 40,000, preferably from about 3000 to about 30,000.

The fluorosilicones useful herein have a molecular weight of from about 200,000 to about 300,000, preferably from about 240,000 to about 260,000 and most preferably about 250,000.

The silicone gums include dimethicones as described by Petrarch and others including U.S. Pat. No. 4,152,416, May 1, 1979 to Spitzer, et al, and Noll, Walter, *Chemistry and Technology of Silicones,* New York: Academic Press 1968. Also describing silicone gums are General Electric Silicone Rubber Product Data Sheets SE 30, SE 33, SE 54 and SE 76. "Silicone gum" materials useful herein denote high molecular weight materials having a mass-average molecular weight in excess of about 200,000 and preferably from about 200,000 to about 4,000,000. Typically, they have a viscosity at 25° C. in excess of about 1,000,000 $mm^2.s^{-1}$. Specific examples include polydimethylsiloxane, (polydimethylsiloxane) (methylvinylsiloxane) copolymer, poly(dimethylsiloxane) (diphenyl) (methylvinylsiloxane) copolymer and mixtures thereof.

The silicone-based carriers suitable for use herein include certain silicone fluids. The silicone fluid can be either a polyalkyl siloxane, a polyaryl siloxane, a polyalkylaryl siloxane or a polyether siloxane copolymer. Mixtures of these fluids can also be used and are preferred in certain executions.

The polyalkyl siloxane fluids that can be used include, for example, polydimethylsiloxanes with viscosities ranging from about 0.65 to 600,000 $mm^2.s^{-1}$, preferably from about 0.65 to about 10,000 $mm^2.s^{-1}$ at 25° C. These siloxanes are available, for example, from the General Electric Company as the Viscasil (RTM) series and from Dow Corning as the Dow Corning 200 series. The essentially non-volatile polyalkylarylsiloxane fluids that can be used include, for example, polymethylphenylsiloxanes, having viscosities of about 0.65 to 30,000 $mm^2.s^{-1}$ at 25° C. These siloxanes are available, for example, from the General Electric Company as SF 1075 methyl phenyl fluid or from Dow Corning as 556 Cosmetic Grade Fluid. Also suitable for use herein are certain volatile cyclic polydimethylsiloxanes having a ring structure incorporating from about 3 to about 7 $(CH_3)_2SiO$ moieties.

The viscosity can be measured by means of a glass capillary viscometer as set forth in Dow Corning Corporate Test Method CTM0004, Jul. 29, 1970. Preferably the viscosity of the silicone blend constituting the secondary oil phase ranges from about 500 $mm^2 \cdot s^{-1}$ to about 100,000 $mm^2.s^{-1}$, preferably from about 1000 $mm^2.s^{-1}$ to about 10,000 $mm^2.s^{-1}$.

The most preferred silicone component for use herein is a dimethiconol gum having a molecular weight of from about 200,000 to about 4,000,000 along with a silicone carrier with a viscosity of about 0.65 to 100 mm$^2$.s$^{-1}$. An example of this silicone component is Dow Corning Q2-1403 (85% 5 mm$^2$.s$^{-1}$ Dimethicone Fluid/1 5% Dimethiconol) and Dow Corning Q2-1401 available from Dow Corning.

Another class of silicone component suitable for use herein include polydiorganosiloxane-polyoxyalkylene copolymers containing at least one polydiorganosiloxane segment and at least one polyoxyalkylene segment, said polydiorganosiloxane segment consisting essentially of $$R_bSiO_{(4-b)/2}$$

siloxane units wherein b has a value of from about 0 to about 3, inclusive, there being an average value of approximately 2 R radicals per silicon for all siloxane units in the copolymer, and R denotes a radical selected from methyl, ethyl, vinyl, phenyl and a divalent radical bonding said polyoxyalkylene segment to the polydiorganosiloxane segment, at least about 95% of all R radicals being methyl; and said polyoxyalkylene segment having an average molecular weight of at least about 1000 and consisting of from about 0 to about 50 mol percent polyoxypropylene units and from about 50 to about 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from about 2 to about 8. Such polymers are described in U.S. Pat. No. 4,268,499.

Preference for use herein are polydiorganosiloxane-polyoxyalkylene copolymers having the general formula:

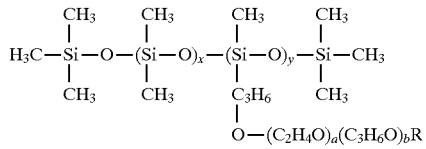

wherein x and y are selected such that the weight ratio of polydiorgano-siloxane segments to polyoxalkalkylene segments is from about 2 to about 8, the mol ratio of a:(a+b) is from about 0.5 to about 1, and R is a chain terminating group, especially selected from hydrogen; hydroxyl; alkyl, such as methyl, ethyl, propyl, butyl, benzyl; aryl, such as phenyl; alkoxy such as methoxy, ethoxy, propoxy, butoxy; benzyloxy; aryloxy, such as phenoxy; alkynyloxy, such as vinyloxy and allyloxy; acyloxy, such as acetoxy, acryloxy and propionoxy and amino, such as dimethylamino.

The number of and average molecular weights of the segments in the copolymer are such that the weight ratio of polydiorganosiloxane segments to polyoxyalkylene segments in the copolymer is preferably from about 2.5 to about 4.0.

Suitable copolymers are available commercially under the tradenames Belsil (RTM) from Wacker-Chemie GmbH, Geschäftsbereich S, Postfach D-8000 Munich 22 and Abil (RTM) from Th. Goldschmidt Ltd., Tego House, Victoria Road, Ruislip, Middlesex, HA4 0YL. Particularly preferred for use herein are Belsil (RTM) 6031 and Abil (RTM) B88183.

The above polydiorganosiloxane-polyoxyalkylene copolymers can be used above or in admixture with other silicones, for example, the volatile cyclic polydimethylsiloxanes. Moreover, such copolymers and mixtures can be used in combination with the herein defined silicone gums.

The silicone component is valuable herein in conjunction with the liquid crystal-forming emulsifier and liquid, polyol carboxylic acid ester for modifying the perceived skin feel of the composition. Highly preferred in this respect are silicone gums having a molecular weight of from 200,000 to 4,000,000. Thus according to another aspect of the invention, there is provided a skin care composition in the form of an oil-in-water dispersion which comprises a silicone or mixture of silicones in a level of from 0.1% to 20% by weight, the silicone or silicone mixture comprising a silicone gum having a molecular weight of from about 200,000 to about 4,000,000 and wherein the composition additionally incorporates from about 0.01% to about 20% of a liquid, polyol carboxylic acid ester having a polyol moiety and at least 4 carboxylic acid moieties, wherein the polyol moiety is selected from sugars and sugar alcohols containing from about 4 to about 8 hydroxyl groups, and wherein each carboxylic acid moiety has from about 8 to about 22 carbon atoms, and wherein said liquid polyol carboxylic acid ester has a complete melting point of less than about 30° C.; and wherein the composition optionally comprises from about 0.1% to about 20% of an emulsifier capable of forming liquid crystals in water, the preferred emulsifier being a fatty acid ester blend based on a mixture of sorbitan fatty acid ester and sucrose fatty acid ester. The fatty acid ester in each instance is preferably $C_8$–$C_{24}$, more preferably $C_{10}$–$C_{20}$. The silicone or silicone mixture is preferably present in a level of from about 0.1% to about 15%, preferably from 0.1% to about 10% by weight of composition, this level being based on the total blend of gum and non-gum silicone materials. In preferred embodiments, the compositions of this aspect of the invention comprise a primary oil phase which is essentially silicone-free together with a secondary oil phase comprising the silicone gum. The primary oil phase is described in detail above.

Preferred embodiments herein comprise from about 0.1% to about 10% by weight of an unsaturated fatty acid or ester. Preferred unsaturated fatty acids and esters for use herein are optionally hydroxy substituted $C_8$–$C_{50}$ unsaturated fatty acids and esters, especially esters of ricinoleic acid. The unsaturated fatty acid or ester component is valuable herein in combination with the liquid crystal-forming emulsifier for improving the skin feel and rub-in characteristics of the compositon. Highly preferred in this respect is cetyl ricinoleate.

An essential oil-phase component of the compositions herein is a polyol ester skin conditioning agent. The compositions of the present invention comprise from about 0.01% to about 20%, preferably from about 0.1% to about 15%, and more preferably from about 1% to about 10% by weight of the polyol ester. The level of polyol ester by weight of the oil in the composition is from about 1% to about 30%, preferably from about 5% to about 20%.

The polyol ester preferred for use herein is a nonocclusive liquid or, liquifiable polyol carboxylic acid ester. These polyol esters are derived from a polyol radical or moiety and one or more carboxylic acid radicals or moieties. In other words, these esters contain a moiety derived from a polyol and one or more moieties derived from a carboxylic acid. These carboxylic acid esters can also be derived from a carboxylic acid. These carboxylic acid esters can also be described as liquid polyol fatty acid esters, because the terms carboxylic acid and fatty acid are often used interchangeably by those skilled in the art.

The liquid polyol polyesters employed in this invention comprise certain polyols, especially sugars or sugar alcohols, esterified with at least four fatty acid groups. Accordingly, the polyol starting material must have at least four esterifiable hydroxyl groups. Examples of preferred polyols are sugars, including monosaccharaides and disaccharides, and sugar alcohols. Examples of monosaccharides containing four hydroxyl groups are xylose and arabinose and the sugar alcohol derived from xylose, which has five hydroxyl groups, i.e., xylitol. The monosaccharide, erythrose, is not suitable in the practice of this invention since it only contains three hydroxyl groups, but the sugar alcohol derived from erythrose, i.e., erythritol, contains four hydroxyl groups and accordingly can be used. Suitable five hydroxyl group-containing monosaccharides are galactose, fructose, and sorbose. Sugar alcohols containing six —OH groups derived from the hydrolysis products of sucrose, as well as glucose and sorbose, e.g., sorbitol, are also suitable. Examples of disaccharide polyols which can be used include maltose, lactose, and sucrose, all of which contain eight hydroxyl groups.

Preferred polyols for preparing the polyesters for use in the present invention are selected from the group consisting of erythritol, xylitol, sorbitol, glucose, and sucrose. Sucrose is especially preferred.

The polyol starting material having at least four hydroxyl groups is esterified on at least four of the —OH groups with a fatty acid containing from about 8 to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty acids; they can be saturated or unsaturated, including positional and geometrical isomers. However, in order to provide liquid polyesters preferred for use herein, at least about 50% by weight of the fatty acid incorporated into the polyester molecule should be unsaturated. Oleic and linoleic acids, and mixtures thereof, are especially preferred.

The polyol fatty acid polyesters useful in this invention should contain at least four fatty acid ester groups. It is not necessary that all of the hydroxyl groups of the polyol be esterified with fatty acid, but it is preferable that the polyester contain no more than two unesterified hydroxyl groups. Most preferably, substantially all of the hydroxyl groups of the polyol are esterified with fatty acid, i.e., the polyol moiety is substantially completely esterified. The fatty acids esterified to the polyol molecule can be the same or mixed, but as noted above, a substantial amount of the unsaturated acid ester groups must be present to provide liquidity.

To illustrate the above points, a sucrose fatty triester would not be suitable for use herein because it does not contain the required four fatty acid ester groups. A sucrose tetra-fatty acid ester would be suitable, but is not preferred because it has more than two unesterified hydroxyl groups. A sucrose hexa-fatty acid ester would be preferred because it has no more than two unesterified hydroxyl groups. Highly preferred compounds in which all the hydroxyl groups are esterified with fatty acids include the liquid sucrose octa-substituted fatty acid esters.

The following are non-limiting examples of specific polyol fatty acid polyesters containing at least four fatty acid ester groups suitable for use in the present invention: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose heptaoleate, sucrose octaoleate, and mixtures thereof.

As noted above, highly preferred polyol fatty acid esters are those wherein the fatty acids contain from about 14 to about 18 carbon atoms.

The preferred liquid polyol polyesters preferred for use herein have complete melting points below about 30° C., preferably below about 27.5° C., more preferably below about 25° C. Complete melting points reported herein are measured by Differential Scanning Calorimetry (DSC).

The polyol fatty acid polyesters suitable for use herein can be prepared by a variety of methods well known to those skilled in the art. These methods include: transesterification of the polyol with methyl, ethyl or glycerol fatty acid esters using a variety of catalysts; acylation of the polyol with a fatty acid chloride; acylation of the polyol with a fatty acid anhydride; and acylation of the polyol with a fatty acid, per se. See U.S. Pat. No. 2,831,854; U.S. Pat. No. 4,005,196, to Jandacek, issued Jan. 25, 1977; U.S. Pat. No. 4,005,196, to Jandacek, issued Jan. 25, 1977.

A second essential ingredient in the composition herein is an organic amphiphilic emusifier material which is capable of forming liquid crystals in product or when the product is applied on the skin at ambient or elevated temperatures. Preferably the emulsifier is capable of forming liquid crystals (especially smectic lyotropic liquid crystals) at a temperature in the range from about 20° C. to about 60° C. The emulsifier is preferably incorporated into the composition in an amount of from about 0.1% to about 20%, preferably from about 0.1% to about 10%, and more preferably from about 0.1% to about 8% by weight of composition. The amphiphilic emulsifier preferred for use herein is selected from polyol esters, alkoxylated polyol esters and mixtures thereof, a preferred emulsifier comprising a sugar ester, especially an ester selected from sucrose oleates and palmitates and mixtures thereof. Preferred polyol and alkoxylated polyol esters are mono-, di-, and tri-ester materials, especially the mono- and di-esters. Highly preferred herein is a fatty acid ester blend based on a mixture of sorbitan or sorbitol fatty acid ester and sucrose fatty acid ester, the fatty acid in each instance being preferably $C_8$–$C_{24}$, more preferably $C_{10}$–$C_{20}$. The preferred fatty acid ester emulsifier from the viewpoint of moisturisation is a blend of sorbitan or sorbitol $C_{16}$–$C_{20}$ fatty acid ester with sucrose $C_{10}$–$C_{16}$ fatty acid ester, especially sorbitan stearate and sucrose cocoate. This is commercially available from ICI under the trade name Arlatone 2121. The stabilisation mechanism of formulation derived from Arlatone 2121 is based on the formation of distinct liquid crystalline structures in the water phase into which the oil phase is dispersed. In order to achieve optimum moisturisation, absorption and skin feel together with reduced greasiness it is desirable for the ratio of primary oil to fatty acid ester emulsifier to lie in the range from about 20:1 to about 1:1, preferably from about 15:1 to about 1:1 and especially from about 13:1 to about 1:1.

A highly preferred ingredient of the compositions herein is urea which is preferably present in a level of from about 0.1% to about 20%, more preferably from about 0.5% to about 10% and especially from about 1% to about 5% by weight of composition.

In preferred embodiments, the oil phase and organic amphiphilic material are premixed in water at a temperature above the Kraft Point of the organic amphiphilic material (but preferably below about 60° C.) to form a liquid crystal/oil in water dispersion prior to addition of the urea. The urea is found to be especially effective herein in combination with the amphiphilic emulsifier material and the polyol fatty acid polyester for providing outstanding skin moisturisation and softening in the context of an oil-in-water skin care emulsion composition. Moreover, it is surprisingly found that the urea is rendered more stable to hydrolytic degradation, thereby allowing an increase in compositional pH.

A wide variety of optional ingredients such as non-occlusive moisturizers, humectants, gelling agents, neutralizing agents, perfumes, colouring agents and surfactants, can be added to the skin compositions herein.

The compositions herein can comprise a humectant. Suitable humectants for use herein include sorbitol, propylene glycol, butylene glycol, hexylene glycol, ethoxylated glucose derivatives, hexanetriol, glycerine, water-soluble polyglycerylmethacrylate lubricants and panthenols. A preferred humectant herein is glycerine (sometimes known as glycerol or glycerin). Chemically, glycerine is 1,2,3-propanetriol and is a product of commerce. One large source of the material is in the manufacture of soap. Glycerine is especially preferred in the compositions of the invention from the viewpoint of boosting moisturisation. Also preferred for use herein is butylene glycol.

In the present compositions, the humectant is preferably present at a level of from about 0.1% to about 20%, more preferably from about 1% to about 15%, and especially from about 5% to about 15% by weight of composition.

Suitable polyglycerylmethacrylate lubricants for use in the compositions of this invention are available under the trademark Lubrajel (RTM) from Guardian Chemical Corporation, 230 Marcus Blvd., Hauppage, N.Y. 11787. In general, Lubrajels can be described as hydrates or clathrates which are formed by the reaction of sodium glycerate with a methacrylic acid polymer. Thereafter, the hydrate or clathrate is stabilized with a small amount of propylene glycol, followed by controlled hydration of the resulting product. Lubrajels are marketed in a number of grades of varying glycerate: polymer ratio and viscosity. Suitable Lubrajels include Lubrajel TW, Lubrajel CG and Lubrajel MS, Lubrajel WA, Lubrajel DV and so-called Lubrajel Oil.

At least part (up to about 5% by weight of composition) of the humectant can be incorporated in the form of an admixture with a particulate lipophilic or hydrophobic carrier material. The carrier material and humectant can be added either to the aqueous or disperse phase.

This copolymer is particularly valuable for reducing shine and controlling oil while helping to provide effective moisturization benefits. The cross-linked hydrophobic polymer is preferably in the form of a copolymer lattice with at least one active ingredient dispersed uniformly throughout and entrapped within the copolymer lattice. Alternatively, the hydrophobic polymer can take the form of a porous particle having a surface area (N$_2$,BET) in the range from about 50 to 500, preferably 100 to 300 m$^{-2}$.g$^{-1}$ and having the active ingredient absorbed therein.

The cross-linked hydrophobic polymer is preferably present in an amount of from about 0.1% to about 10% by weight and is preferably incorporated in the external aqueous phase. The active ingredient can be one or more or a mixture of skin compatible oils, skin compatible humectants, emollients, moisturizing agents and sunscreens. In one embodiment, the polymer material is in the form of a powder, the powder being a combined system of particles. The system of powder particles forms a lattice which includes unit particles of less than about one micron in average diameter, agglomerates of fused unit particles of sized in the range of about 20 to 100 microns in average diameter and aggregates of clusters of fused agglomerates of sizes in the range of about 200 to 1,200 microns in average diameter.

The powder material of this embodiment can be broadly described as a cross-linked "post absorbed" hydrophobic polymer lattice. The powder preferably has entrapped and dispersed therein, an active which may be in the form of a solid, liquid or gas. The lattice is in particulate form and constitutes free flowing discrete solid particles when loaded with the active material. The lattice may contain a predetermined quantity of the active material. A suitable polymer has the structural formula:

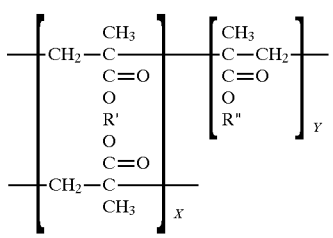

where the ratio of x to y is 80:20, R' is —CH$_2$CH$_2$— and R" is —(CH$_2$)$_{11}$CH$_3$.

The hydrophobic polymer is a highly crosslinked polymer, more particularly a highly cross-linked polymethacrylate copolymer. The material is manufactured by the Dow Corning Corporation, Midland. Mich., USA, and sold under the trademark POLYTRAP (RTM). It is an ultralight free-flowing white powder and the particles are capable of absorbing high levels of lipophilic liquids and some hydrophilic liquids while at the same time maintaining a free-flowing powder character. The powder structure consists of a lattice of unit particles less than one micron that are fused into agglomerates of 20 to 100 microns and the agglomerates are loosely clustered into macro-particles or aggregates of about 200 to about 1200 micron size. The polymer powder is capable of containing as much as four times its weight of fluids, emulsions, dispersion or melted solids.

Adsorption of actives onto the polymer powder can be accomplished using a stainless steel mixing bowl and a spoon, wherein the active is added to the powder and the spoon is used to gently fold the active into the polymer powder. Low viscosity fluids may be adsorbed by addition of the fluids to a sealable vessel containing the polymer and then tumbling the materials until a consistency is achieved. More elaborate blending equipment such as ribbon or twin cone blenders can also be employed. The preferred active ingredient for use herein is glycerine. Preferably, the weight ratio of humectant: carrier is from about 1:4 to about 3:1.

Also suitable as a highly cross-linked polymethacrylate copolymer is Microsponges 5647. This takes the form of generally spherical particles of cross-linked hydrophobic polymer having a pore size of from about 0.01 to about 0.05 μm and a surface area of 200–300 m$^2$/g. Again, it is preferably loaded with humectant in the levels described above.

The compositions of the invention can also contain a hydrophilic gelling agent at a level preferably from about 0.01% to about 10%, more preferably from about 0.02% to about 2%, and especially from about 0.02% to about 0.5%. The gelling agent preferably has a viscosity (1% aqueous solution, 20° C., Brookfield RVT) of at least about 4000 mPa.s, more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylpyrrolidone, polyvinylalcohol, guar gum, hydroxypropyl guar gum and xanthan gum.

Preferred hydrophilic gelling agents herein, however, are acrylic acid/ethyl acrylate copolymers and the carboxyvinyl polymers sold by the B. F. Goodrich Company under the trade mark of Carbopol resins. These resins consist essentially of a colloidally water-soluble polyalkenyl polyether crosslinked polymer of acrylic acid crosslinked with from 0.75% to 2.00% of a crosslinking agent such as for example polyallyl sucrose or polyallyl pentaerythritol. Examples include Carbopol 934, Carbopol 940, Carbopol 950, Carbopol 954, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. A most preferred polymer is Carbopol 954. Also suitable for use herein are hydrophobically-modified cross-linked polymers of acrylic acid having amphipathic properties available under the Trade Name Carbopol 1382, Carbopol 1342 and Pemulen TR-1 (CTFA Designation: Acrylates/10–30 Alkyl Acrylate Crosspolymer). A combination of the polyalkenyl polyether cross-linked acrylic acid polymer and the hydrophobically modified cross-linked acrylic acid polymer is also suitable and is preferred for use herein. The gelling agents herein are particularly valuable for providing excellent stability characteristics over both normal and elevated temperatures.

Neutralizing agents suitable for use in neutralizing acidic group containing hydrophilic gelling agents herein include sodium hydroxide, potassium hydroxide, ammonium hydroxide, monoethanolamine, diethanolamine and triethanolamine.

The compositions of the invention are in emulsion form and are preferably formulated so as to have a product viscosity of at least about 4,000 mPa.s and preferably in the range from about 4,000 to about 300,000 mPa.s, more preferably from about 8,000 to about 200,000 mPa.s and especially from about 10,000 to about 100,000 mPa.s and even more especially from about 10,000 to about 50,000 mPa.s (25° C., neat, Brookfield RVT Spindle No. 5).

The compositions of the invention can also contain from about 0.1% to about 10%, preferably from about 1% to about 5% of a panthenol moisturizer. The panthenol moisturizer can be selected from D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, pantoyl lactose and Vitamin B complex. Highly preferred from the viewpoint of skin care and tack reduction is D-panthenol.

The compositions of the present invention can additionally comprise from about 0.001% to about 0.5%, preferably from about 0.002% to about 0.05%, more preferably from about 0.005% to about 0.02% by weight of carboxymethylchitin. Chitin is a polysaccharide which is present in the integument of lobsters and crabs and is a mucopolysaccharide having beta (1–4) linkages of N-acetyl-D-glucosamine. Carboxymethylchitin is prepared by treating the purified chitin material with alkali followed by monochloracetic acid. It is sold commercially in the form of a dilute (approximately 0.1% to 0.5% by weight) aqueous solution under the name Chitin Liquid available from A & E Connock Ltd., Fordingbridge, Hampshire, England.

Other optional materials include keratolytic agents such as salicylic acid; proteins and polypeptides and derivatives thereof; water-soluble or solubilizable preservatives such as Germall 115, methyl, ethyl, propyl and butyl esters of hydroxybenzoic acid, benzyl alcohol, EDTA, Euxyl (RTM) K400, Bromopol (2-bromo-2-nitropropane-1,3-diol) and phenoxypropanol; anti-bacterials such as Irgasan (RTM) and phenoxyethanol (preferably at levels of from 0.1% to about 5%); soluble or colloidally-soluble moisturising agents such as hylaronic acid and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076, 663; colouring agents; perfumes and perfume solubilizers and additional surfactants/emulsifiers such as fatty alcohol ethoxylates, ethoxylated polyol fatty acid esters, wherein the polyol can be selected from glycerine, propyleneglycol, ethyleneglycol, sorbitol, sorbitan, polypropyleneglycol, glucose and sucrose. Examples include glyceryl monohydroxy stearate and stearyl alcohol ethoxylated with an average of from 10 to 200 moles of ethyleneoxide per mole of alcohol and PEG-6 caprylic/capric glycerides.

Also useful herein are sunscreening agents. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*. Preferred among those sunscreens which are useful in the compositions of the instant invention are those selected from 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.

Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVB radiation range. These sunscreening agents provide higher efficacy, broader UV absorption, lower skin penetration and longer lasting efficacy relative to conventional sunscreens. Especially preferred examples of these sunscreens include those selected from 4-N,N-(2-ethylhexyl) methyl-aminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl) methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206–38269, Aug. 25, 1978.

The compositions of the present invention can additionally comprise from about 0.1% to about 5% by weight of aluminium starch octenylsuccinate. Aluminium starch octenylsuccinate is the aluminium salt of the reaction product of octenylsuccinic anhydride with starch and is commercially available under the trade name from Dry Flo National Starch & Chemical Ltd. Dry Flo is useful herein from the viewpoint of skin feel and application characteristics.

Other optional materials herein include pigments which, where water-insoluble, contribute to and are included in the total level of oil phase ingredients. Pigments suitable for use in the compositions of the present invention can be organic and/or inorganic. Also included within the term pigment are materials having a low colour or lustre such as matte finishing agents, and also light scattering agents. Examples of suitable pigments are iron oxides, acyglutamate iron oxides, ultramarine blue, D&C dyes, cannine, and mixtures thereof. Depending upon the type of composition, a mixture of pigments will normally be used. The preferred pigments for use herein from the viewpoint of moisturisation, skin feel, skin appearance and emulsion compatibility are treated pigments. The pigments can be treated with compounds such as amino acids, silicones, lecithin and ester oils.

The pH of the compositions is preferably from about 4 to about 9, more preferably from about 6 to about 8.0. The water content of the compositions herein is generally from about 30% to about 98.89%, preferably from about 50% to about 95% and especially from about 60% to about 90% by weight.

The invention is illustrated by the following examples

Examples I to V

|  | I/% | II/% | III/% | IV/% | V/% |
| --- | --- | --- | --- | --- | --- |
| Cetyl Alcohol | 0.25 | 0.3 | 0.2 | 0.3 | 0.25 |
| Stearic Acid | 0.11 | 0.2 | 0.1 | 0.2 | 0.1 |
| Steareth 100 | 0.1 | 0.1 | 0.15 | 0.15 | 0.15 |
| GMHS (1) | 0.15 | 0.2 | 0.1 | 0.2 | 0.15 |
| Cetyl Palmitate | 3.0 | 2 | 3 | 4 | 2.5 |
| Mineral Oil | 2.0 | 3 | 4 | 3 | 3.5 |
| Petrolatum | 3.00 | 2 | 2.5 | 4 | 3.5 |
| Wickenol 142 (RTM) | 0.60 | 1 | 1 | 1 | 0.7 |
| Dimethicone 200 | 0.3 | 0.4 | 0.5 | 0.5 | 0.4 |
| Propyl Paraben | 0.08 | 0.08 | 0.07 | 0.08 | 0.07 |
| Arlatone (RTM) 2121 | 1.0 | 2.0 | 1.5 | 1.0 | 4.0 |
| Glycerin | 10 | 9 | 8 | 11 | 9 |
| Carbopol (RTM) 1342 | 0.095 | 0.075 | 0.075 | 0.075 | 0.075 |
| Carbopol (RTM) 951 | 0.09 | 0.08 | 0.09 | 0.09 | 0.08 |
| Na4 EDTA | 0.1 | 0.2 | 0.1 | 0.1 | 0.1 |
| Methyl Paraben | 0.175 | 0.175 | 0.175 | 0.175 | 0.175 |
| KOH | 0.3 | 0.2 | 0.2 | 0.2 | 0.2 |
| Dimethicone Q21403 | 1.0 | — | 0.5 | 2.0 | — |
| CeRiccinoleate | — | 0.5 | — | 1 | — |
| Butylene Glycol | — | — | — | 2 | — |
| DryFlo (RTM) | — | — | — | 0.5 | — |
| Perfume | 0.2 | 0.2 | — | 0.2 | — |
| Urea | 2.5 | 1.5 | 3 | 2 | 2.5 |
| SPE (2) | 2.0 | 1.0 | 2.5 | 2.0 | 2.2 |
| Colour | 0.0004 | 0.0002 | 0.0003 | — | — |
| Water | to 100 | to 100 | to 100 | to 100 | to 100 |

1. Glycerylmonohydroxystearate
2. Liquid sucrose polyester which is a mixture of hexa-, hepta-, and octa-sucrose esters, predominately the octa-ester esterified with mixed soybean oil fatty acids.

The compositions are made as follows:

A first premix of thickening agents, Arlatone 2121, and other water soluble ingredients apart from urea, is prepared by admixing in water and heating to about 80° C. A second premix of oil phase ingredients other than silicone gum is prepared by mixing and heating and is added to the aqueous premix.

The resulting mixture is cooled to about 60° C. The silicone gum component and urea are then added to the resulting oil-in-water emulsion and the mixture is cooled before adding minor ingredients. The composition is ready for packaging.

The compositions display improved moisturisation, skin feel and skin care characteristics together with reduced greasiness and excellent rub-in and absorption characteristics.

We claim:

1. A skin care composition in the form of an oil-in-water emulsion comprising:
    (a) from about 1% to about 60% by weight of oil phase components comprising from about 0.01% to about 20% by weight of a liquid, polyol carboxylic acid ester selected from the group consisting of sucrose pentaoleate, sucrose hexaoleate, sucrose heptaoleate, sucrose octaoleate, and mixtures thereof, having a complete melting point of less than about 30° C.;
    (b) from about 30% to about 98.89% by weight of water;
    (c) from about 0.1% to about 20% by weight of an organic liquid crystal-forming amphiphilic emulsifier material, wherein the emulsifier is a blend of sorbitan stearate and sucrose cocoate; and
    (d) from about 0.1% to about 20% by weight of urea.

2. A skin care composition according to claim 1 wherein the oil and organic amphiphilic emulsifier material are premixed in water to form a liquid crystal/oil in water dispersion prior to addition of the urea.

3. A skin care composition according to claim 2 wherein the composition comprises from about 0.5% to about 10%, by weight of urea.

4. A skin care composition according to claim 1 comprising from about 2% to about 30% by weight of oil and from about 0.1% to about 10% by weight of amphiphilic emulsifier material.

5. A skin care composition according to claim 1 comprising one or more distinct oil phases and wherein the primary oil phase is essentially silicone-free and is present in a level of from about 4% to about 16% by weight and wherein the weight ratio of primary oil phase to emusifier is in the range from about 20:1 to about 1:1.

6. A skin care composition according to claim 5 wherein the primary oil phase comprises a natural or synthetic oil selected from the group consisting of mineral, vegetable, and animal oils, fats and waxes, fatty acid esters, fatty alcohols, fatty acids and mixtures thereof.

7. A skin care composition according to claim 5 incorporating a secondary oil phase which comprises a silicone or mixture of silicones in a level of from 0.1% to 20% by weight by weight of composition, and wherein the silicone or silicone mixture comprises a silicone gum having a molecular weight of from about 200,000 to about 4,000,000.

8. A composition according to claim 1 wherein said liquid polyol carboxylic acid ester has a complete melting point below about 27.5° C.

9. A composition according to claim 1 wherein said liquid polyol carboxylic acid polyester has a complete melting point below about 25° C.

10. A skin care composition according to claim 1 additionally comprising from about 0.1% to 10% of an optionally hydroxy substituted $C_8$–$C_{50}$ unsaturated fatty acid or an ester thereof.

11. A skin care composition according to claim 10 wherein the optionally hydroxy substituted $C_8$–$C_{50}$ unsaturated fatty acid or ester thereof is cetyl ricinoleate.

12. A skin care composition according to claim 1 additional comprising from about 0.1% to about 20% by weight of a humectant selected from the group consisting of glycerine, polyglycerylmethacrylate lubricants, butylene glycol, sorbitol, panthenols, propylene glycol, hexylene glycol, hexanetriol, glucose ethers, and mixtures thereof.

13. A skin care composition according to claim 12 wherein the humectant is selected from the group consisting of glycerine, butylene glycol, and mixtures thereof.

14. A skin care composition according to claim 1 additionally comprising from about 0.01% to about 10% by weight of a hydrophilic gelling agent selected from the group consisting of carboxyvinyl polymers.

15. A skin care composition according to claim 14 wherein the gelling agent comprises a hydrophobically-modified cross-linked polymer of acrylic acid having amphipathic properties.

16. A skin care composition according to claim 3 wherein the composition comprises from about 1% to about 5% by weight of urea.

17. A skin care composition according to claim 4 comprising from about 3% to about 20% by weight of oil and from about 0.1% to 10% by weight of amphiphilic emulsifier material.

18. A skin care composition according to claim 4 comprising from about 2% to about 30% by weight of oil and from about 0.1% to about 8% by weight of amphiphilic emulsifier material.

19. A skin care composition according to claim 18 comprising from about 3% to about 20% by weight of oil and from about 0.1% to about 8% by weight of amphiphilic emulsifier material.

20. A skin care composition according to claim 5 comprising one or more distinct oil phases and wherein the primary oil phase is essentially silicone-free and is present in a level of from about 4% to about 16% by weight and wherein the weight ratio of primary oil phase to emulsifier is in the range from about 15:1 to about 1:1.

21. A skin care composition according to claim 7 incorporating a secondary oil phase which comprises a silicone or mixture of silicones in a level of from 0.1% to about 15% by weight of composition, and wherein the silicone or silicone mixture comprises a silicone gum having a molecular weight of from about 200,000 to about 4,000,000.

22. A skin care composition according to claim 21 incorporating a secondary oil phase which comprises a silicone or mixture of silicones in a level of from 0.1% to about 10% by weight of composition, and wherein the silicone or silicone mixture comprises a silicone gum having a molecular weight of from about 200,000 to about 4,000,000.

23. A skin care composition according to claim 14 wherein the carboxyvinyl polymer is selected from the group consisting of colloidally water-soluble polymers of acrylic acid cross-linked with from about 0.75% to about 2% of a cross-linking agent selected from the group consisting of polyalkyl sucrose and polyalkyl pentaerythritol.

* * * * *

UNITED STATES PATENT AND TRADEMARK OFFICE
CERTIFICATE OF CORRECTION

PATENT NO.    :    5,871,760

DATED         :    February 16, 1999

INVENTOR(S)   :    Darrell Gene Doughty et al.

It is certified that error appears in the above-identified patent and that said Letters Patent is hereby corrected as shown below:

At column 1, line 17 "by 8 mn" should read --by 8 nm--.

At column 2, line 36 "bums" should read --burns--.

At column 5, line 4 "Fluid/1 5%" should read --Fluid/15%--.

At column 6, line 56 "or, liquifiable" should read --or liquifiable--.

At column 9, line 51 "300 m$^{-2}$.g-$^{1}$" should read -- $300\ m^2.g^{-1}$ --

At column 10, line 25 "Dow Coming" should read --Dow Corning--.

At column 12, line 43 "UVB radiation" should read --UVA radiation--.

At column 13, line 12 "cannine" should read --carmine--.

At column 14, lines 62-63 "additional" should read --additionally--.

Signed and Sealed this

Nineteenth Day of October, 1999

*Attest:*

Q. TODD DICKINSON

*Attesting Officer*    *Acting Commissioner of Patents and Trademarks*